Figure 1:
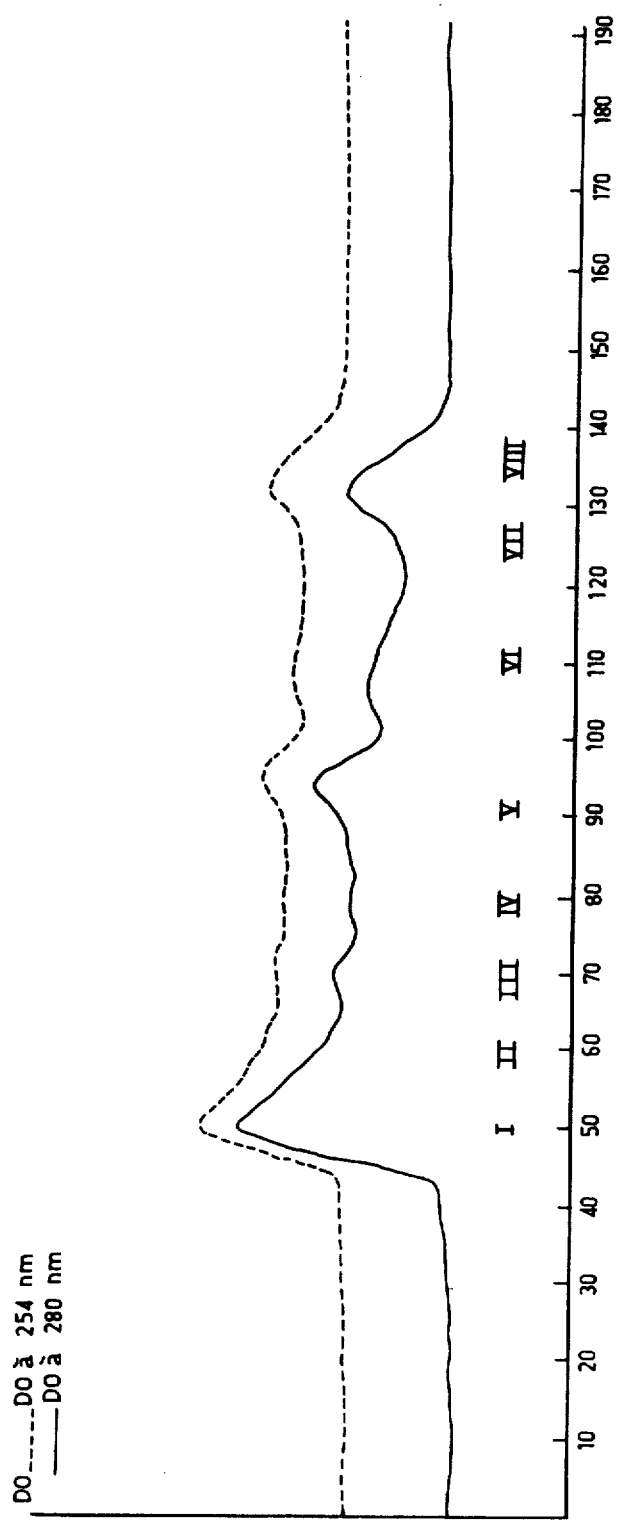

United States Patent [19]

Jolles et al.

[11] Patent Number: 4,462,990

[45] Date of Patent: Jul. 31, 1984

[54] BIOLOGICALLY ACTIVE SUBSTANCES, THEIR OBTAINMENT FROM HUMAN CASEIN AND COMPOSITIONS CONTAINING SAID SUBSTANCES

[75] Inventors: Pierre Jolles, Paris; Danièle Migliore-Samour, Le Kremlin Bicetre, all of France

[73] Assignee: Institut National de la Sante et de la Recherche Medicale, Paris, France

[21] Appl. No.: 385,645

[22] PCT Filed: Oct. 2, 1981

[86] PCT No.: PCT/FR81/00126

§ 371 Date: May 21, 1982

§ 102(e) Date: May 21, 1982

[87] PCT Pub. No.: WO82/01131

PCT Pub. Date: Apr. 15, 1982

[30] Foreign Application Priority Data

Oct. 3, 1980 [FR] France .................................. 80 21292

[51] Int. Cl.$^3$ ...................... A61K 37/00; C07G 7/00; C07C 103/52; C12P 21/06
[52] U.S. Cl. ............................. 424/177; 260/112 R; 260/112.5 R; 435/69
[58] Field of Search .................... 424/177; 435/69; 260/112.5 R, 112 R

[56] References Cited

U.S. PATENT DOCUMENTS

| | | | |
|---|---|---|---|
| 1,631,887 | 6/1927 | Posternak | 435/69 |
| 1,658,289 | 2/1928 | Heidlberg | 435/69 |
| 3,186,918 | 6/1965 | Salzberg et al. | 435/69 |
| 3,323,929 | 6/1967 | Salzburg et al. | 435/69 |
| 3,558,770 | 1/1971 | Gordon et al. | 424/177 |
| 4,358,465 | 11/1982 | Brule et al. | 435/69 |
| 4,361,587 | 11/1982 | Brule et al. | 435/69 |

FOREIGN PATENT DOCUMENTS

| | | | |
|---|---|---|---|
| 1411478 | 9/1965 | France | 424/177 |
| 1466141 | 5/1966 | France | 424/177 |
| 1461423 | 9/1966 | France | 424/177 |

OTHER PUBLICATIONS

Biol. Abstr. 74, p. 64855.
Journal of Dairy Science, 54, No. 7, pp. 987–993, (1970).

*Primary Examiner*—Delbert R. Phillips
*Attorney, Agent, or Firm*—Oblon, Fisher, Spivak, McClelland & Maier

[57] ABSTRACT

New biologically active substances obtained by treating human casein with trypsin then fractionating and optionally purifying. They have immunological properties.

8 Claims, 2 Drawing Figures

BIOLOGICALLY ACTIVE SUBSTANCES, THEIR OBTAINMENT FROM HUMAN CASEIN AND COMPOSITIONS CONTAINING SAID SUBSTANCES

The present invention relates to biologically active substances obtained by fractionating enzymatic hydrolysates of the human casein and the compositions containing these substances.

The use of casein derivatives in biological compositions has already been proposed. In this respect, the following patents may be cited:

French Pat. No. 1,461,423 which relates to a biological composition for treating human skin; this composition comprises, either in the acid form or in the salt form, the chemical combination obtained by the association of the carbonyl group derived from the carboxyl group of palmitic acid with the aminated, imidazolic, phenolic and hydroxylated functions of the fractions of the chemically- or enzymatically-hydrolysed caseins.

French Pat. No. 1,466,141 which relates to biological substances for preparing detergent compositions for corporal use. These detergent compositions are characterized by the presence of acylated amino-acids or acylates peptides, or the mixture of both. Among the suitable acylated peptides are mentioned in particular caseinic acids substituted by a fatty acid residue.

U.S. Pat. No. 3,558,770 relating to wound treating compositions which contain a casein modified by the action of an enzyme.

French Pat. No. 1,411,478 which relates to a composition for protecting the skin against the aggressivity of solvents and various hydrophobic substances. This composition comprises a gelling substance of animal origin (for example casein) or of vegetable origin or of purely chemical origin, a partial or total hydrolysate of animal or vegetable proteins, a substance having a surface active character and a small amount of a chemical detergent.

There may also be mentioned as documents illustrating the state of the art, French Pat. Nos. 1,518,665 and 7,810,857.

It will be observed that all the compositions described in the aforementioned patents are essentially compositions for topical use, in particular for cosmetic purposes or for hygiene of the skin in which are present derivatives of casein obtained for example by enzymatic hydrolysis, said derivatives being coupled with lipidic fractions by chemical synthesis. This lipidic coupling imparts the desired topical activity to the casein derivatives. Nothing indicates that these derivatives come from human casein and that the fractionation of these derivatives, independently of any coupling with a lipidic fraction, would result in substances having an immunological activity, i.e. substances whose field of application and mode of administration are totally different from those described in the aforementioned prior art.

The presently claimed invention permits the obtainment, by the fractionation of human casein which has been subjected to the action of a proteolytic enzyme, of biologically active substances which are immunological agents stimulating in particular the formation of antibodies.

The human casein, which is a complex of proteins ($\alpha_s$, $\beta$, $\kappa$, ...), is present essentially in maternal milk. Under the action of a proteolytic enzyme, the casein may produce after fractionation biologically active substances.

According to the present invention, the new substances are obtained by the treatment, with at least one proteolytic enzyme, of human casein which was delipidated and rendered soluble, followed by the fractionation of the hydrosoluble products, as a function of their mean molecular weight, by filtration on a suitable support.

The new substances according to the invention has a mean molecular weight of between 1000 and 5500. Of most particular interest are the substances according to the invention whose mean molecular weight is in the neighbourhood of 1200±200; however, the substances whose mean molecular weight is in the neighbourhood of 2500 or 5500 also have interesting properties.

As a proteolytic enzyme there is advantageously employed in the process of the invention, trypsin, chymotrypsin, or some other analogous enzyme, or mixtures thereof, the trypsin being preferred.

As a suitable support, there may be employed in particular a column of Sephadex G 50.

There will be mentioned merely by way of example that the fractionation on a column of Sephadex G 50 of the hydrosoluble fraction coming from the treatment of human casein delipidated and rendered soluble by trypsin for twenty-four hours at 37° C., gives three biologically active fractions namely the substances IV, V, and VI which will be defined hereinafter in example 1.

It has also been found that the subsequent purification of the substance V under suitable conditions on a column of DEAE-Sephadex A-25 allows to isolate different products and to select those whose immunological properties are improved over those of the "substance V" itself.

Thus, depending on the composition and pH of the elution solvent, there were isolated by filtration of the substance V on DEAE-Sephadex A-25:

a substance of "basic or neutral" character, named "MJH-24" by using as the eluent a buffer solution having a pH in the neighbourhood of 8, then substances of an "acid" character, named MJH-63 and MJH-65, by using as an eluent a buffer solution having a pH in the neighbourhood of 3.5.

Preferably, there is employed as a buffer solution a "TRIS" buffer [tris (hydroxymethyl)amino methane] having different pHs, to which is optionally added a mineral salt such as sodium chloride.

The filtration on the column of DEAE-Sephadex A-25 is followed by measuring the absorption at 280 nm of the collected fractions. The active substances obtained after this subsequent purification are isolated, for example, after dialysis then lyophilisation of their aqueous solution. It has been determined that the substance MJH-24 is a pentapeptide which contains the following five amino acids; serine, proline, leucine, phenylalanine and histidine.

Further, the substances obtained according to the fractionating process of the present invention may be, if desired, coupled with fatty acids. Generally, the fatty acids are aliphatic acids containing 8 to 18 carbon atoms. Lauric acid is of a particular interest. The coupling may be effected by treating a substance according to the present invention with an activated derivative of a fatty acid such as the anhydride or the chloride.

The new substances according to the present invention and their products of coupling with the fatty acids are immunological agents which stimulate the formation of antibodies and accelerate the phagocytosis phenomenon.

In vitro, they were found to be particularly active at concentrations of between 0.1 and 10 μg/ml in the test of the secretion of anti-(sheep red-cells)antibodies by the splenic cells of mice immunized in vivo and in the test of phagocytosis of sheep red cells opsonized by the peritoneal macrophages of mice.

The following examples, which are intended to be non-limitative, show how the invention can be carried out.

EXAMPLE 1

The human casein (400 mg) is delipidated by treatment with 25 ml of a chloroform-methanol mixture (2:1 by volume).

The insoluble casein is solubilized by treatment with a 0.05 N sodium hydroxide solution in such manner that the final concentration of casein is in the neighbourhood of 2 mg/cm$^3$.

The obtained solution is subjected to a dialysis against 2 liters of a buffer 0.033 M phosphate having a pH 8 for 2 days by renewing the buffer solution 5 times.

A solution having a pH 8 and containing the soluble casein is so obtained. This solution is subjected to the action of trypsin so that the ratio enzyme/substrate is in the neighbourhood of 1/100. The enzymatic hydrolysis is continued for 24 hours at 37° C., one half of the amount of enzyme being introduced at the beginning of the reaction and the remainder 4 hours after the beginning of the hydrolysis.

The reaction mixture is centrifuged at 15,000 rpm for 2 hours; the supernatent is dried and 16 ml of a 30% acetic acid solution are added. The mixture is subjected to 3 successive centrifugations at 13,000 rpm for 30 minutes.

The clear supernatent liquid (16 ml) is filtred on a column of Sephadex G 50 (height: 105 cm, diameter 2.5 cm), the eluent being 30% acetic acid and fractions of 2 cc being collected.

In operating in this manner and following the chromatography by U.V. absorption, zones are obtained which permit the definition of 8 fractions in respect of which the mean molecular weight is established. The diagram of the filtration is shown in FIG. 1.

The biologically active fractions are the following:

Substance IV: fractions 71 to 82; mean molecular weight 5,300.

Substance V: fractions 84 to 98, mean molecular weight 2,230.

Substance VI: fractions 99 to 114; mean molecular weight 1,120.

EXAMPLE 2

Each of the substances obtained in example 1 is subjected to the action of lauric anhydride by operating in tertiary butyl alcohol.

For each of the lipid substances, there are obtained a fraction soluble in tertiary butyl alcohol and a fraction insoluble in tertiary butyl alochol.

Each of these fractions is subjected to biological tests: the insoluble lipid fraction IV and the insoluble lipid fraction VI have properties of particular interest.

EXAMPLE 3

467 mg of the "fraction V", obtained in example 1, are filtered on a column of DEAE-Sephadex A-25 (height:127 cm; diameter 1.9 cm)and fractions of 2.3 cm$^3$ are collected.

The filtration is carried out in the following manner:

(a) elution with a buffer solution TRIS, HCl 0.01 M, pH 8:276 fractions are collected among which the fractions 120 to 132 provide with the substance MJH-24.

(b) elution with a buffer solution TRIS, 0.01 M HCl, pH 3.5 and 0.1 N sodium chloride: 164 fractions are collected and eliminated (fractions 276 to 440).

(c) elution with a buffer solution TRIS, 0.01 M HCl, pH 3.5 and 0.5 N sodium chloride: 220 fractions (fractions 440 to 660)are collected among which the fractions 543 to 553 and the fractions 571 to 604 respectively provide the active substances MJH-63 and MJH-65.

Figure 2:
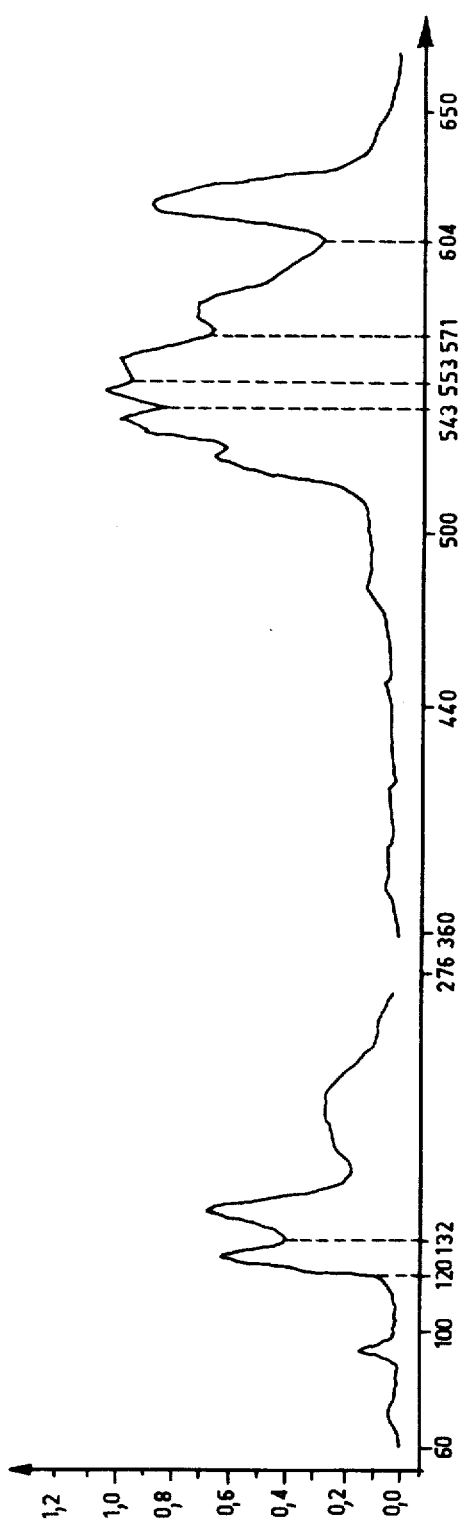

The filtration diagram is shown in FIG. 2 in which the numbers of the fractions are plotted as abscissae and the optical densities at 280 nm are plotted as ordinates.

The substances MJH-24, MJH-63, and MJH-65 thus obtained have to a higher degree the properties of the active hydrosoluble substance from which they are derived (fraction V). In vitro, they stimulate the formation of antibodies and accelerate the phagocytosis.

In addition, the substances MJH-24, MJH-63 and MJH-65 exhibit in the mouse a remarkable activity beyond the dose of 0.05 mg/kg i.v. as concerns the experimental infection pneumonic klebsiella.

The present invention also relates to compositions of use in therapeutics which contain a substance according to the present invention associated with one or more compatible and pharmaceutically acceptable diluents or adjuvants.

The compositions may be employed as vaccine adjuvants (for example anti-influenza vaccine composed of hemagglutin in sub-units, anti-poliomyelitis vaccine having an inactivated virus, anti-malaria vaccine) and in a simultaneous injection with the antigen (viral, bacterial, parasitic, fungal tumoural) in respect of which it is desired to increase the production of antibodies or the specific cellular reactivity.

These pharmaceutical compositions may also be employed as non-specific immunostimulants for increasing the resistance of the host(man or domestic animal) as concerns infections or in anti-tumoural immunotherapy.

By way of adjuvants, the products may be administered as an aqueous solution or an oily emulsion, or in the form of liposome with the antigen in respect of which it is desired to obtain an increased or improved immunity response by the route employed for this antigen and in proportions varying from 0.01 to 10 times the amount of antigen with which they are mixed before being injected.

In respect of the application as a non-specific immunostimulant, these products may be employed by the intravenous, intramuscular, subcutaneous, intranasal, possibly oral or rectal route, in aqueous solution or in oily emulsion or in the form of liposomes. In this case, the dosage of the compound according to the invention administered is usually between 0.01 and 25 mg/kg. In human therapeutics, the daily dosages depend on the desired effect. They may be between 0.01 and 10 mg for an adult.

The solid compositions for oral administration may be tablets, pills, powders or granules.

As liquid compositions for oral administration, there may be employed pharmaceutically acceptable emulsions, solutions, suspensions, syrups, elixirs.

The compositions for parenteral or intranasal administration may be aqueous sterile solutions, suspensions, or emulsions.

The sterilization may be carried out in several ways, for example by means of a bacteriological filter or by incorporation of sterilizing agents. The solid compositions rendered sterile by irradiation ($\beta$-rays) may be dissolved in sterile water or any other injectable sterile medium, if desired at the moment of use.

The compositions for rectal administration are suppositories.

The following non-limitative example 4 illustrates a composition according to the invention.

EXAMPLE 4

There is prepared in the normal way a liquid composition administrable by the intravenous route having the following composition:

| | |
|---|---|
| Substance V obtained in example 1 | 50 mg |
| Injectable solution | 5 ml |

EXAMPLE 5

There is prepared in the usual way a liquid composition administrable by the intravenous route having the following composition:

| | |
|---|---|
| Substance MOH-63 obtained in example 1 | 50 mg |
| Injectable solution | 5 ml |

What we claim is:

1. A process for obtaining new biologically active immunological substances which stimulate the formation of antibodies and accelerate the phagocytosis phenomenon, which comprises treating a delipidated soluble human casein with at least one proteolytic enzyme selected from trypsin and chymotrypsin, the ratio enzyme/substrate being in the neighborhood of 1/100 for 24 hours at 37° C., then, after centrifugation, fractionating the hydrosoluble products as a function of their mean molecular weight by filtration on a suitable support with 30% acetic acid as eluant, and then isolating the biologically active substances comprising:

(a) substance IV having a mean molecular weight of 5,300;

(b) substance V having a mean molecular weight of 2,230; and (c) substance VI having a mean molecular weight of 1,120.

2. The process of claim 1 wherein substance V is subsequently filtered on a suitable column with, as eluant, a buffer solution whose pH decreases, and isolating a substance of basic character named MJH-24 and substances of acidic character named MJH-63 and MJH-65, said substance of basic character being isolated after elution with a buffer solution of TRIS and 0.01 M HCl at pH 8, and said substances of acidic character being isolated after elution with a buffer solution of TRIS and 0.01 M HCl at pH 3.5 which is 0.1 N sodium chloride, and then with a buffer solution of TRIS and 0.01 M HCl at pH 3.5 which is 0.5 N sodium chloride.

3. A process according to claim 1, characterized in that it further comprises reacting the active substances obtained after filtration with a fatty acid.

4. A process according to claim 3, characterized in that the fatty acid is in an activated derivative form.

5. New biologically active immunological substances obtained by the process of claim 1.

6. New biologically active immunological substances obtained by the process of claim 2.

7. A biologically active immunological pharmaceutical composition, characterized in that it contains an effective amount of at least one substance according to claim 5, associated with one or more compatible diluents or adjuvants.

8. A biologically active immunological pharmaceutical composition, characterized in that it contains an effective amount of at least one substance according to claim 6, associated with one or more compatible diluents or adjuvants.

* * * * *